United States Patent [19]

Ogino et al.

[11] Patent Number: 4,933,506

[45] Date of Patent: Jun. 12, 1990

[54] PROCESS FOR THE PRODUCTION OF DIHYDRIC PHENOLS

[75] Inventors: Takao Ogino, Iwakuni; Shunji Arita, Otake; Masayuki Takeda, Yamaguchi; Masaru Kaya, Iwakuni, all of Japan

[73] Assignee: Mitsui Petrochemical Industries, Ltd., Tokyo, Japan

[21] Appl. No.: 274,901

[22] Filed: Nov. 22, 1988

[30] Foreign Application Priority Data

Dec. 7, 1987 [JP] Japan ............................. 62-309247

[51] Int. Cl.$^5$ ............................................ C07C 37/08
[52] U.S. Cl. ................................... 568/768; 568/771; 568/741
[58] Field of Search ................ 568/768, 771, 798, 741

[56] References Cited

U.S. PATENT DOCUMENTS 4,283,570 8/1981 Nakagawa et al. ................. 568/768

FOREIGN PATENT DOCUMENTS 2737302 2/1978 Fed. Rep. of Germany .
0150529 9/1978 Japan .
910735 11/1962 United Kingdom ................. 568/768

*Primary Examiner*—Werren B. Lone
*Attorney, Agent, or Firm*—Sherman and Shalloway

[57] ABSTRACT

A process for the production of dihydric phenoles by oxidizing diisopropylbenzenes, which comprises oxidizing diisopropylbenzenes with molecular oxygen to obtain a reaction product mixture (A) containing at least diisopropylbenzene dihydroperoxide (DHP) and diisopropylbenzene monocarbinol monohydroperoxide (HHP), supply said product mixture (A) in a form of oily phase as a solution in an aromatic hydrocarbon solvent to an agitation reactor, supplying thereto at the same time, as an aqueous phase, hydrogen peroxide at a feed rate of 1-5 moles per mole of HHP contained in the product mixture and an acid catalyst in an amount sufficient to reach a concentration in the aqueous phase of 10-40% by weight, the concentration of hydrogen peroxide in the aqueous phase being maintained at a value of at least 20% by weight and the weight ratio of the oily phase/aqueous phase being at least 10, causing oxidization of the HHP into DHP by hydrogen peroxide while maintaining the reaction temperature at 30°-60° C. to obtain a reaction product mixture (B), separating the aqueous phase from the oily phase in the reaction product mixture (B) and subjecting the DHP in the so separated oily phase to an acid cleavage to form corresponding dihydric phenol. The process permits to dispense with the removal of the reaction water, recirculation of the aromatic hydrocarbon and of the aqueous phase, while allowing a higher ratio of oily phase/aqueous phase and thus allowing reduction of the requisite amount of hydrogen peroxide and of the acid catalyst with simultaneous decrease in the reaction time.

8 Claims, 2 Drawing Sheets

PROCESS FOR THE PRODUCTION OF DIHYDRIC PHENOLS

BACKGROUND OF THE INVENTION

1. Field of the invention

The present invention relates to a process for the production of dihydric phenols, such as resorcin etc., in particular, by oxidizing diisopropylbenzenes followed by acid cleavage of the resulting dihydroperoxides.

2. Desrciption of the Prior Art

It has been known that hydroperoxides, such as, diisopropylbenzene dihydroperoxide (DHP), diisopropylbezene monocarbinol monohydroperoxide (HHP), diisopropylbezene monohydroperoxide (MHP) and so on, are produced together with carbinols, such as, diisopropylbezene dicarbinol (DC) and so on, by oxidizing diisopropylbezenes with molecular oxygen in the presence of a base.

It has also been well known that industrially useful chemicals, such as, resorcin, hydroquinone and so on, can be obtained by subjecting DHP to an acid cleavage using an acid catalyst, such as, sulfuric acid or so on, in the presence of an aromatic hydrocarbon solvent, such as toluene etc., or a ketone solvent, such as, acetone, methyl isobutyl keytone (MIBK) or so on.

While these prior techniques can be employed as a useful process for obtaining resorcin and hydroquinone from diisopropylbezene, there has been a strong demand for producing hydroperoxides, especially DHPs at higher yeild by oxidizing diisopropylbezene more efficiently in order to obtain resorcin or hydroquinone at a more higher over-all yield from diisopropylbezene.

Attempts had been proposed for converting the carbinols, such as, HHP, DC etc., present in the reaction product mixture of the oxidation of diisopropylbezene further into DHP by oxidizing them by contacting the product mixture with hydrogen peroxide ($H_2O_2$), as disclosed, for example, in the British Patent No. 910,735, in the Japanese Patent Application Lay Open Nos. 23939/1978, 53265/1980 and so on. According to the disclosures of the above Japanese Patent Application Lay Open Nos. 23939/1978 and 53265/1980, it is taught that dihydric phenols can be obtained in a high efficiency by oxidizing carbinols, such as, HHP, DC and so on, with subsequent acid cleavage of the oxidation products, by conducting the process step of oxidization of the carbinols into DHPs with hydrogen peroxide separately from the process step of acid cleavage of the DHPs into the corresponding dihydric phenols.

In summary, the prior technique for the production of dihydric phenols, such as resorcin etc., by oxidzing isopropylbezenes with subsequent acid cleavage of the oxidation product proposed previously has been based on the following reaction scheme:

Upon oxidizing diisopropylbenzenes with molecular oxygen in the presence of a base using, if necessary, a radical initiator, a reaction mixture containing DHP, HHP, MHP, DC and so on as explained above is obtained. This oxidation product mixture is then subjected to a further oxidation with hydrogen peroxide in order to oxidize HHP, DC and so on contained in the product mixture into DHP in a heterogeneous reaction system consisting of an oily phase of an aromatic hydrocarbon solvent, such as toluene etc., containing dissolved therein said oxidation product mixture and of an aqueous phase containing hydrogen peroxide and an acid catalyst, such as sulfuric acid, by contacting the two phases with each other. Then, the so formed DHP is subjected to an acid cleavage in a separate process step to convert it into the corresponding dihydric phenol, such as resorcin or so on.

The process step of oxidizing the HHP, DC and so on with hydrogen peroxide into DHPs may be realized by supplying the product mixture of oxidization of diisopropylbenzene in a form of an oil phase containing said product mixture in an aromatic hydrocarbon solvent, such as toluene etc., to a tank reactor equipped at its top with a distillation column and a water separator, while supplying to this reactor simultaneously hydrogen peroxide and an acid catalyst, such as sulfuric acid, in a form of aqueous phase, so as to cause the two phases to contact with each other in order to effect oxidation of the said HHP, DC etc., by hydrogen peroxide at a temperture of 20°-70° C. Then, the oily phase in the resulting reaction mixture is separated from the aqueous phase and the aqueous phase is recirculated to the reactor under supplement of the consumed hydrogen peroxide and the acid catalyst, while the oily phase is supplied to the subsequent acid cleavage step after it has been neutralized and concentrated. It was proposed to supply hydrogen peroxide to the reactor in an amount of about 16 moles per mole of HHP. Here, the weight ratio of oily phase to aqueous phase in the reactor is maintained at a value of about 1.6. The reaction water formed by the oxidation of HHP is removed fromm the reaction mixture by an azeotropic distillation with the aromatic hydrocarbon under a reduced pressure to the outside of the system, wherein the aromatic hydrocarbon is recirculated to the reactor. In the above procedure, it is necessary to maintain the reaction temperature by supplying vapor of an inert solvent for avoiding any detrimental influence due to localized heating. The reason why the ratio of oily phase/aqueous phase is to be maintained at about 1.6 in the reactor is such that the acid cleavage of the peroxide will scarcely occur when an ample aqueous phase is present, even if a concentrated acid catalyst resulting from the concentration of the aqueous phase may come to contact with the reaction liquor. However, use of large amount of water is not preferable, since predominant part of the by-products is transferred to the aqueous phase which accumulate therein after repeated recirculation cycles. In addition, it is necessary to maintain the concentration of hydrogen peroxide in the reaction system at about 16 times of HHP in mole ratio due to employment of large amount of water.

Thus, the prior technique of oxidizing HHP, DC and so on by hydrogen peroxide into DHPs has disadvantages, since quite large amount of hydrogen peroxide relative to the amount of HHP etc., should be supplied and laborious and uneconomical procedures of dehydration by an azeotropic distillation under a reduced pressure and recirculation of the aromatic hydrocarbon are necessary, beside the necessity of controlling the concentrations of hydrogen peroxide and of the acid catalyst for the requisite recirculation of the aqueous phase with simultaneous demand of large amount of water for maintaining the ratio of oily phase/aqueous phase at a lower value in oder to conduct the operation smoothly.

SUMMARY OF THE INVENTION

An object of the present invention is to obviate the above disadvantages and to provide a novel process for the production of dihydric phenols which permits to dispense with the removal of the reaction water, recirculation of the aromatic hydrocarbon and of the aqueous phase, while allowing a higher ratio of oily phase/aqueous phase and thus allowing reduction of the requisite amount of hydrogen peroxide and of the acid catalyst with simultaneous decrease in the reaction time.

The novel process for the production of dihydric phenols according to the present invention comprises steps of:

oxidizing diisopropylbenzenes with molecular oxygen to obtain a reaction product mixture (A) containing at least diisopropylbenzene dihydroperoxide (DHP) and diisopropylbenzene monocarbinol monohydroperoxide (HHP), supplying said reaction product mixture (A) in a form of an oily phase as a solution in an aromatic hydrocarbon solvent to an agitation reactor, supplying thereto at the same time, as an aqueous phase, hydrogen peroxide at a feed rate of 1-5 moles per mole of HHP contained in the reaction mixture (A) and an acid catalyst in an amount sufficient to reach a concentration in the aqueous phase of 10-40% by weight, the concentration of hydrogen peroxide in the aqueous phase being maintained at a value of at least 20% by weight and the weight ratio of the oily phase/aqueous phase being at least 10, causing oxidization of the HHP into corresponding DHP by hydrogen peroxide while maintaining the reaction temperture at 30°-60°C. to obtain a reaction product mixture (B), separating the aqueous phase from the oily phase in the reaction product mixture (B) and subjecting the DHP in the so separated oily phase to acid cleavage to form corresponding dihydric phenol.

DETAILED DESCRIPTION OF THE INVENTION

In the process for the production of dihydric phenols according to the present invention, hydrogen peroxide and the acid catalyst are supplied to an agitation reactor in a form of aqueous phase, wherein the feed rate of hydrogen peroxide is such that the amount of hydrogen peroxide will be 1-5 moles per mole of HHP contained in the product mixture (A) and the concentration of the acid catalyst in the aqueous phase is maintained at 10-40% by weight, whereupon the oily phase and the aqueous phase are brought into contact with each other to cause the HHP etc. in the product mixture (A) to be oxidized into corresponding DHPs under such a condition that the concentration of hydrogen peroxide in the aqueous phase is kept to be at least 20% by weight and the weight ratio of oily phase/aqueous phase is maintained at a value of at least 10, without specifically reducing the pressure. Therefore, there is no occurrence of concentration of acid catalyst in the aqueous phase and, at the same time, recirculation of aromatic hydrocarbon solvent can be dispensed with. Moreover, in the case of no repeated use of the aqueous phase, there is no need for adjusting or controlling the concentration of hydrogen peroxide and of the acid catalyst with simultaneous permission of reduction of the requisite amount thereof.

In this specification, the dihydric phenols are meant to include, beside resorcin, hydroquinone and so on, also those having substituents, such as alkyl etc. The same applies also to the diisopropylbenzenes, DHPs, HHPs, DC and so on.

In the process according to the present invention, the oxidation of a diisopropylbenzene by molecular oxygen is first effected to form an oxidation product mixture (A) containing at least diisopropylbenzene dihydroperoxide (DHP) and diisopropylbenzene monocarbinol monohydroperoxide (HHP).

For the oxidation of diisopropylbenzenes (DIPBs) with molecular oxygen to produce DHPs and HHPs, any process widely known hitherto can be employed. In general, the oxidation of diisopropylbenzenes (DIPBs) by molecular oxygen, such as air, is effected in the presence of a base using, if necessary, a radical initiator. Upon this oxidation of DIPBs with molecular oxygen, by-products such as, diisopropylbenzene dicarbinol (DC), diisopropylbenzene monohydroperoxide (MHP) and so on are formed besides DHP and HHP.

Figure 1:
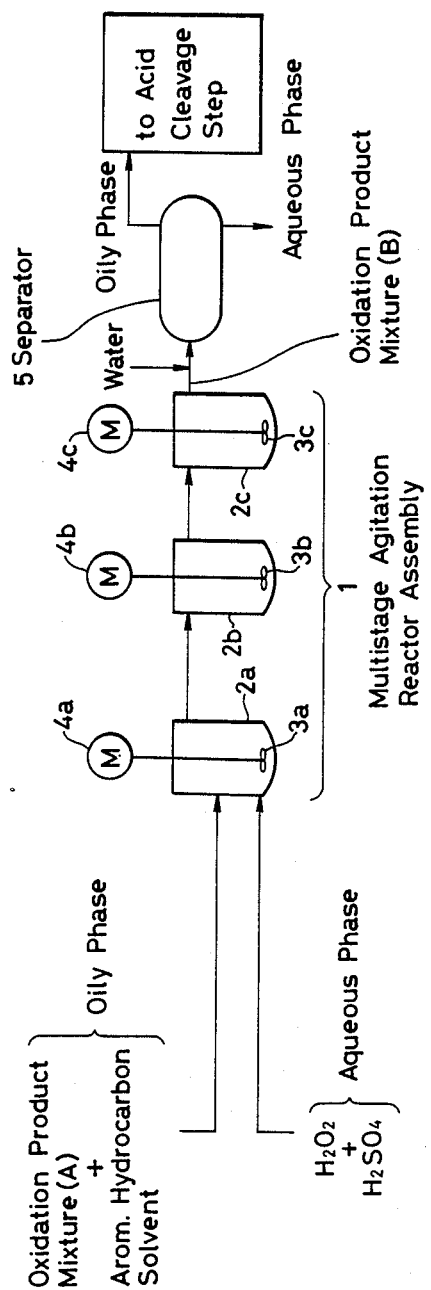
FIGS. 1 and 2 show each a flow chart of preferable embodiment of the process according to the present invention.
Figure 2:
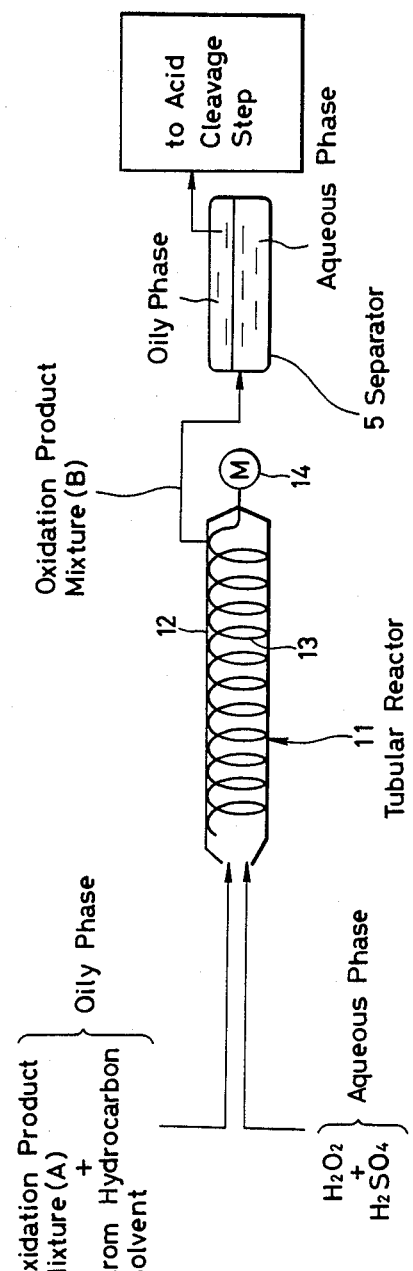

Then, the so obtained oxidation product mixture (A) is dissolved in an aromatic hydrocarbon solvent to form an oily phase and the alkaline aqueous phase is separated off, whereupon the thus formed oily phase is supplied to an agitation reactor arrangement, such as, a multistage agitation reactor assembly 1 as shown in the appened FIG. 1 or to a tubular reactor 11 as shown in the appended FIG. 2. The multistage agitaion reactor assembly 1 shown in FIG. 1 consists of several agitation reactors 2a, 2b, 2c ... cascadingly connected in series in multistages each equipped with an agitation device 3a, 3b, 3c ... driven by a motor 4a, 4b, 4c ... for the agitation device 3a, 3b, 3c ..., those which rotate at a revolution rate corresponding to a peripheral speed of at least 1 m/sec may be preferable. The tubular reactor 11 as shown in FIG. 2 is provided with a rotatable coil 13 which is disposed in a horizontal tube 12 and is driven by a motor 14.

For the aromatic hydrocarbon solvent for dissolving the oxidation product mixture (A), there may be enumerated, for example, benzene, toluene, xylene, ethylbenzene, cumene, cymene, diisoprpylbenzene and so on, among which toluene is most preferable.

To the multistage agitation reactor assembly 1 or to the tubular reactor 11, hydrogen peroxide is supplied at a rate corresponding to 1-5 moles, preferably 1.0-3 moles per mole of HHP contained in the oxidation product mixture (A). Thereto is supplied simultaneously an acid catalyst in such an amount that the concentration thereof in the aqueous phase will be 10-40% by weight. The concentration of hydrogen peroxide in the aqueous phase supplied to the reactor assembly 1 or the tubular reactor 11 may be at least 20% by weight, preferably 40-55% by weight. Here, the weight ratio of the oily phase to the aqueous phase within the reactor 1 or 11 may preferably be at least 10, in particular, wihtin the range from 20-35.

For the acid catalyst, inorganic acids, such as, sulfuric acid, hydrochloric acid, perchloric acid, phosphoric acid and so on may be employed, among which sulfuric acid is particularly preferabl.

In the process according to the present invention, the weight ratio of the oily phase to the aqueous phase in the reactor 1 or 11 is settled at a value of at least 10, preferably from 20 to 35, which is quite high as compared with that in the conventional techniques. This means that the amount of aqueous phase in the reactor 1 or 11 is considerably small. Therefore, it is now made possible to settle the amount of hydrogen peroxide employed for the oxidation of HHP present in the oxidation product mixture (A) at a considerably low level as low as 1–5 moles per mole of HHP. It is also made possible to choose a concentration of hydrogen peroxide in the aqueous phase supplied to the reactor 1 or 11 at a value of at least 20% by weight, preferably in the range from 40 to 55% by weight.

The oxidation of HHP contained in the oxidation product mixture (A) by hydrogen peroxide is effected while maintaining the temperature of the reaction system containing these reactants at 30°–60° C., preferably at a temperture in the range from 40° to 55° C., to obtain DHP. Here, it is preferable to maintain the reaction mixture in the reactor under an intensively agitated condition.

In the process according to the present invention, the reaction liquor is held in an agitated state using an agitation reactor arrangement to effect the oxidation efficiently. Examples of such agitation reactor arrangement include:

(1) a tank reactor with mechanical agitation equipped with an ordinary agitation device, such as, a stirrer having varying form of agitation vane (for example, turbine type, curved paddles, inclined paddles and so on) or with a high speed rotary shearing stirrer, such as, Homomixer (trademark) of the firm Tokushu-Kika Kogyo K. K. or so on, and (2) a tubular reactor in which the reaction liquor flows inside the reactor tube in a turbulent flow.

The agitation condition of the mechanical agitation reactor of above (1) according to the present invention implies a peripheral speed of the rotary agitation vane transmitting the agitation energy directly to the reaction liquor of at least 1 m/sec, preferably at least 5 m/sec. Here, the peripheral speed as used in this specification is expressed by the value calculated by $r \times \omega$, assuming r to be the distance from the center of rotation to the outer-most periphery of the rotating vane in m and $\omega$ to be the angular velocity of the vane in radian/sec.

In the process according to the present invention, it is more advantageous to realize the oxidation of HHP etc. in the product mixture (A) with hydrogen peroxide in a multistage system than in a single stage system, if the oxidation reaction is performed in a continous process.

While the reaction time may be different in accordance with the reaction temperature, concentration of the acid catalyst, concentration of hydrogen peroxide and so on, it varies, in particular, by the condition of agitation. Thus, a reaction time of 10–30 minutes is usually necessary at a peripheral speed of the agitation device of 1.1 m/sec, while it may be reduced consiberably by increasing the peripheral speed an may amount to, for example, 3–15 minutes at a peripheral speed of 3.8 m/sec and 0.5–5 minutes at a peripheral speed of 11 m/sec.

In the process according to the present invention, the problem of acid cleavage of aromatic hydroperoxide which is assumed to be due to the evaporation of water at the interface between the liquid phase and the gas phase can be avoided by fully charging the agitation reactor with the reaction liquor, wherein the internal temperature can be adjusted by flowing hot water through the surrounding water jacket.

In the tubular reactor of above (2), the reaction liquor is flown through the reactor tube in a turbulent flow in order to facilitate the agitation of the reaction liquor within the reactor tube. A turbulent flow of the reaction liquor in the tubular reactor can be attained by selecting the rate of the reaction liquor appropriately. It is possible, if necessary, to install a rotatable coil within the reactor tube for effecting mechanical agitation to facilitate the turbulence of the reaction liquor flowing inside the tube. The critial condition between turbulent flow and laminar flow may be discriminated, as well known in the art, by calculating the Reynolds number (Re) from the flow velocity. The accepted critical Reynolds number for a non-obstructed flow path lies at about 2,000, above which a turbulent condition occurs.

For a circular tube, Reynolds number, which is a dimensionless number, is calculated by the following equation:

$$Re = \frac{d \cdot U \cdot \rho}{\mu}$$

in which d represents the inner diameter of the tube, U is the average flow velocity of the fluid, $\rho$ is density of the fluid and $\mu$ is the viscosity of the fluid.

In the case of tubular reactor, the inner diameter of the reactor tube may, in general, be 10–100 mm, with the average flow velocity of the reaction liquor of, usually, 0.1–5.0 m/sec. The length of the reactor tube may, in general, be in the range from 10 to 500 m, which may be determined appropriately taking into account of the residence time of the liquor therein.

When mechanical agitation reactor mentioned previously is employed, the amount of hydrogen peroxide required for the oxidation reaction can be reduced and, in addition, the reaction time may also be decreased as compared with the case where no such mechanical agitation device is employed.

Now, the oxidation product mixture (B) resulting from the above oxidation by hydrogen peroxide is subject to separation of the oily phase from the aqueous phase in the separator 5 shown in FIG. 1 or 2 after addition of, if necessary, an amount of water for termination of the oxidation reaction. The thus separated oily phase is then, if necessary, neutralized and concentrated and fed to the acid cleavage step, in order subject the DHPs contained in the oily phase to an acid cleavage to convert it into corresponding dihydric phenols, such as resorcin and so on.

For effecting the acid cleavage of DHPs contained in the oily phase, any of the conventional techniques known hitherto may be applied. Thus, the acid cleavage may be realized at a temperature of 40°–100° C., preferably 60°–90° C., by adding to the oily phase a ketone solvent, such as, acetone, methyl ethyl ketone and diethyl ketone, and adjusting the concentration of the acid catalyst at a value in the range from 0.001 to 15% by weight.

As the acid catalyst, there may be employed, for example, inorganic acids, such as, sulfuric acid, sulfuric acid anhydride, hydrofluoric acid, perchloric acid, hydrochloric acid, phosphoric acid and so on; strongly acidic ion-exchange resin; solid acids, such as, silicaalumina; organic acids, such as, chloroacetic acid, methanesulfonic acid, bemzenesulfonic acid, p-toluenesulfonic acid and so on; heteropolyacids, such as, phosphowolframic acid, phosphomolybdic acid and so on.

In the process for the production of dihydric phenols according to the present invention, hydrogen peroxide and the acid catalyst are supplied, as explained above, to an agitation reactor as an aqeuous phase at such a rate that the amount of hydrogen peroxide will be 1–5 times, based on mole ratio, of the amount of HHP contained in the product mixture (A) supplied also thereto as an oily phase and the concentration of the acid catalyst in the aqueous phase will be 10–40% by weight, whereupon the oily phase and the aqueous phase are brought into contact with each other to cause oxidation of HHP etc. by hydrogen peroxide into corresponding DHPs under such a condition that the concentration of hydrogen peroxide in the aqueous phase is kept to be at least 20% by weight and the weight ratio of oily phase/aqueous phase is maintained at a value of at least 10, without specifically reducing the pressure. Therefore, no concentration of acid catalyst in the aqueous phase occurs and, at the same time, recirculation of aromatic hydrocarbon solvent can be dispensed with. Moreover, in the case of no repeated use of the aqueous phase, there is no need for adjusting or controlling the concentration of hydrogen peroxide and of the acid catalyst with simultaneous permission of reduction of the requisite amount thereof. Furthermore, the employment of an agitation reactor capable of realizing a powerful agitation affords a marked reduction of the reaction time in the oxidation of the product mixture (A) with hydrogen peroxide with simultaneous increase in the over/all yield of DHPs.

DETAILED DESCRIPTION OF THE PREFERRED EMBODIMENTS

In the following, the present invention will further be described in more detail by way of Examples and Comparison Examples. Here, it is to be emphasized that these specific Examples should not be understood as restrictive to the scope of the invention in any sence.

REFERENCE EXAMPLE 1 m-diisopropylbenzene was oxidized with air in the presence of an aqueous solution sodium at a temperature of 100°C. After the oxidation, toluene was added to the product mixture to cause phase separtion. By removing the so separated alkaline aqueous phase, a toluene solution of th eoxidation product mixture (A) having the composition given in the following Table 1 was obtained.

TABLE 1

| Composition of the Product Mixture (A) | |
| --- | --- |
| Component | Proportion (wt. %) |
| DHP | 24.5 |
| HHP | 7.2 |
| DC | 0.9 |
| MHP | 3.5 |
| Toluene | 59.3 |

EXAMPLES 1 TO 3 AND COMPARISON EXAMPLE 1

To a multistage agitation reactor assembly as shown in FIG. 1, there was supplied the toluene solution (an oily phase) of the oxidation product mixture (A) obtained in the above Reference Example 1 at a rate of 549 parts by weight per hour and, at the same time, an aqueous phase containing hydrogen peroxide and sulfuric acid was supplied thereto at each specific rate as given in Table 2 which is calculated from the conditions given also in Table 2. The oxidation reaction was performed continuously while maintaining the peripheral speed of the agitation device, reaction temperature and the reaction time at each value as given in Table 2 respectively. The oxidation product liquor [oxidation product mixture (B)] derevered from the outlet of the reactor was subjected to separation of the oily phase from the aqueous phase and concentration of the hydroperoxides in the oily phase was analyzed. From this analysis, each yield of DHP was determined. The results are summarized in Table 2. Here, the flow of the aqueous phase was realized in "once-through" and no recirculation thereof was incorporated.

Yield of DHP = 100 × $\frac{\text{Moles of DHP in product liquor}}{\text{Moles of starting (DHP + HHP)}}$ (mole %)

EXAMPLES 4 AND 5

To a tubular reactor as shown in FIG. 2 having arranged internally a rotatable coil (tube inner diameter = 10 mm, tube length = 1 m, revolution rate of the coil = 2,000 r.p.m.), the toluene solution (oily phase) of the oxidation product mixture (A) obtained in Reference Example 1 was supplied at a rate of 549 parts by weight per hour, while supplying thereto at the same time an aqueous phase containing hydrogen peroxide and sulfuric acid at a rate given in Table 2 which is calculated from the conditions given also in Table 2. Oxidation reaction was effected in a continuous manner while maintaining the reaction temperature and the reaction time at each value as given in Table 2. The reaction product mixture (B) delivered from the outlet of the reactor was subjected to separation of the oily phase from the aqueous phase and concentration of the hydroperoxides in the oily phase was anaylzed. The yield of DHP was determined from this analysis. The results are summarized also in Table 2.

COMPARISON EXAMPLE 2

To a tank reactor with mechanical agitation equipped at the top with a distillation column and a water separator and at the lower portion thereof with a gas injection pipe, the toluene solution of the oxidation product mixture (A) obtained in Reference Example 1 was supplied at a rate of 549 parts by weight per hour, while supplying thereto simultaneously an aqueous phase containing hydrogen peroxide and sulfuric acid each in a concentration given in Table 2 at a rate of 449 parts by weight per hour with concurrent introduction of heated vapor of toluene from the gas injection pipe at a rate of 161 parts per hour. The oxidation was effected while maintaining the conditions as to the reaction tempertature and the average residence time (reaction time) at each value given in Table 2 under a pressure of 150 Torr. The entire amount of toluene in the effluent product stream discharged form the top of the reactor was recirculated again to the reaction system, while a part of the aqueous phase separated from the effluent stream was removed to the outside of the system. The reaction product mixture was extracted continuously from the overflow line and was subjected to separation of the oily phase from the aqueous phase, whereupon the aqueous phase was recirculated to the system after the concentrations of hydrogen peroxide and of sulfuric acid had been readjusted to the values given in Table 2. Here, the amount of $H_2O_2$ in the reaction system was 16 times of the amount of HHP in mole ratio due to the recirculation of the aqueous phase, though the amount of $H_2O_2$ requisite for converting the net amount of HHP into DHP were 3.0 times of HHP. By analyzing the oily phase after the reaction, the DHP yield was determined. The results are summarized also in Table 2.

TABLE 2

| Example or Comp. Example No. | Type of Reactor | Periph. Speed of Agitat. Device (m/sec) | Reaction Time (min.) | Reaction Temp. (°C.) | Aqueous Phase $H_2O_2$ Conc. (wt. %) | Aqueous Phase $H_2SO_4$ Conc. (wt. %) | Weight Ratio O/W *1 | Feed Rate of $H_2O_2$ *2 | Consumption of $H_2O_2$ *3 | DHP Yield (mole %) |
|---|---|---|---|---|---|---|---|---|---|---|
| Exam. 1 | 3-Stage Mechanical Agitation Reactor Assembly | 1.1 | 15 | 49 | 48 | 19 | 27 | 1.5 | 1.5 | 87 |
| Exam. 2 | 3-Stage Mechanical Agitation Reactor Assembly | 3.8 | 5 | 49 | 48 | 19 | 27 | 1.5 | 1.5 | 89 |
| Exam. 3 | 3-Stage Mechanical Agitation Reactor Assembly | 11 | 1.5 | 49 | 48 | 19 | 27 | 1.5 | 1.5 | 90 |
| Comp. Exam. 1 | 3-Stage Mechanical Agitation Reactor Assembly | 0.85 | 15 | 49 | 48 | 19 | 27 | 1.5 | 1.5 | 85 |
| Exam. 4 | Tubular Reactor | — | 15 | 50 | 50 | 15 | 29 | 1.5 | 1.5 | 86 |
| Exam. 5 | " | — | 30 | 45 | 48 | 19 | 28 | 1.5 | 1.5 | 87 |
| Comp. Exam. 2 | Tank Reactor with Mechanical Agitation | — | 10 | 49 | 24 | 12 | 1.6 | 16 | 3.0 | 88 |

Notes:
*1 Weight ratio of the oily phase/aqueous phase
*2 Feed rate = [moles of $H_2O_2$ in aq. phase supplied]/[mole of HHP in oily phase supplied]
*3 Mole ratio of $H_2O_2$/HHP As shown in Table 2, the over-all DHP yields for Examples 1-3 were compared to that of Comparison Example 2. Therefore, it is clear that the performances realized by Examples 1-3 are superior in respect of apparatus, processibility, amount of hydrogen peroxide and of the acid catalyst and so on. It is furthermore made clear that the reaction time can be reduced for the case where the peripheral speed of the agitation device is over 1 m/sec by comparing the results of Examples 1-3 with those of Comparison Example 1.

We claim:

1. A process for the production of m-dihydric phenols comprising the process steps of
   oxidizing m-diisopropylbenzenes with molecular oxygen to obtain a reaction product mixture (A) containing at least m-diisopropylbenzene dihydroperoxide (DHP) and m-diisopropylbenzene monocarbinol monohydroperoxide (HHP),
   supplying said reaction product mixture (A) in a form of an oily phase as a solution in an aromatic hydrocarbon solvent to an agitation reactor,
   supplying thereto at the same time, as an aqueous phase, hydrogen peroxide at a feed rate of 1-5 moles per mole of HHP contained in the mixture (A) and an inorganic acid catalyst in an amount sufficient to reach a concentration in the aqueous phase of 10-40% by weight, the concentration of hydrogen peroxide in the aqueous phase being maintained at a value of at least 20% by weight and the weight ratio of the oily phase/aqueous phase being at least 10,
   causing oxidation of the HHP into corresponding DHP by hydrogen peroxide while maintaining the reaction temperature at 30°-60° C. while agitating the resulting reaction mixture at a peripheral speed of at least 1 m/sec without removing the resulting reaction water under reduced pressure to obtain a reaction product mixture (B),
   separating the aqueous phase from the oily phase in the reaction product mixture (B) and
   subjecting the DHP in the so separated oily phase to acid cleavage in the presence of a ketone solvent and a mineral acid catalyst to form corresponding m-dihydric phenol,
   wherein the reaction is effected in a once-through mode without recycling the separated aqueous phase.

2. A process according to claim 1, wherein the agitation reactor is equipped with a mechanical rotary agitation means having a peripheral speed of at least 1 m/sec.

3. A process according to claim 1 or 2, wherein the agitation reactor is equipped with a high speed rotary shearing agitator.

4. A process according to claim 1, wherein the agitation reactor consists of a tubular reactor in which the reaction liquor flows through the reaction tube under a turbulent condition.

5. A process according to either one of claims 1, 2 or 4, wherein two or more agitation reactors are empolyed in a cascading connection.

6. The process according to claim 1 wherein hydrogen peroxide is supplied at a feed rate of 1.0-3 moles per mole of HHP contained in the reaction mixture (A).

7. The process according to claim 1 or 6 wherein the concentration of hydrogen peroxide in the aqueous phase is maintained at a value of from 40 to 55% by weight and the weight ratio of the oily phase/aqueous phase is within the range of from 20 to 35.

8. The process according to claim 1 wherein the mineral acid is sulfuric acid.

* * * * *